United States Patent
Hassler et al.

(10) Patent No.: US 6,436,146 B1
(45) Date of Patent: Aug. 20, 2002

(54) IMPLANT FOR TREATING AILMENTS OF A JOINT OR A BONE

(75) Inventors: Michel Hassler, Saint Ismier; Jean-Pierre Pequignot, Nice; Cécile Real; Olivier Huet, both of Grenoble, all of (FR)

(73) Assignee: Bioprofile, Grenoble (FR)

( * ) Notice: Subject to any disclaimer, the term of this patent is extended or adjusted under 35 U.S.C. 154(b) by 0 days.

(21) Appl. No.: 09/484,880

(22) Filed: Jan. 18, 2000

Related U.S. Application Data

(63) Continuation of application No. 08/988,496, filed on Dec. 10, 1997, now Pat. No. 6,090,145.

(51) Int. Cl.$^7$ .................................................. A61F 2/42
(52) U.S. Cl. ................................. 623/21.11; 623/18.11; 623/23.6
(58) Field of Search ............................ 623/18.11, 19.11, 623/20.11, 20.14, 20.18, 20.32, 20.33, 20.35, 21.11, 21.12, 21.13, 21.14, 21.15, 21.16, 21.19, 22.11, 22.21, 22.4, 23.11, 23.6

(56) References Cited

U.S. PATENT DOCUMENTS

| | | | | |
|---|---|---|---|---|
| 3,526,005 A | | 9/1970 | Bokros et al. ................. | 623/21 |
| 3,707,006 A | | 12/1972 | Bokros et al. .................... | 3/1 |
| 4,005,163 A | | 1/1977 | Bokros ......................... | 264/81 |
| 4,164,793 A | | 8/1979 | Swanson ....................... | 128/92 |
| 4,166,292 A | * | 9/1979 | Bokros .................... | 623/21.18 |
| 4,198,712 A | | 4/1980 | Swanson ....................... | 128/92 |
| 4,259,752 A | * | 4/1981 | Taleisnik .................. | 623/21.13 |
| 4,784,661 A | * | 11/1988 | Beckenbaugh et al. .. | 623/21.12 |
| 4,936,860 A | | 6/1990 | Swanson ....................... | 623/21 |
| 4,955,915 A | | 9/1990 | Swanson ....................... | 623/21 |
| 5,314,485 A | * | 5/1994 | Judet ........................ | 623/21.13 |
| 5,326,364 A | | 7/1994 | Clift, Jr. et al. .............. | 623/21 |
| 5,702,472 A | * | 12/1997 | Huebner .................. | 623/21.15 |
| 5,743,918 A | | 4/1998 | Calandruccio et al. ........ | 623/21 |
| 5,780,119 A | | 7/1998 | Dearnaley et al. .......... | 427/528 |
| 5,782,926 A | | 7/1998 | Lamprecht .................... | 623/21 |

OTHER PUBLICATIONS

High–Strength high–surface–area, porous carbon made from submicron–diameter carbon filaments, Cabon, vol. 34, Issue 9, 1996 pp. 1162.

Commercial brochure entitled "Scaphoid Partial Implant: An Alternative to Arthrodesis" presnted at a Paris trade fair on Dec. 12, 1996.

J.P. Pequignot et al., "Partial Prosthesis of Scaphoid from Silastic to Pyrocarbon", Fourth Congress of F.E.S.S.H., Bologna, Italy, Jun. 1997.

* cited by examiner

Primary Examiner—David J. Isabella
(74) Attorney, Agent, or Firm—St. Onge, Steward, Johnston & Reens, LLC

(57) ABSTRACT

The implant has at least one contact surface portion, made of pyrolytic carbon, designed to be in mobile contact with at least one bony surface when the implant is implanted in a patient. Furthermore, the implant is free from any attaching means, so that it remains free with respect to the at least one bony surface when implanted in the patient.

33 Claims, 12 Drawing Sheets

IMPLANT FOR TREATING AILMENTS OF A JOINT OR A BONE

This is a continuation of Ser. No. 08/988,496 filed Dec. 10, 1997 now U.S. Pat. No. 6,090,145.

BACKGROUND OF THE INVENTION

The present invention generally relates to an implant intended to be implanted between bony surfaces of a patient. Such an implant may replace a defective and painful joint or bone.

According to a particular application of the invention, the implant is used for treating ailments of the scaphoid (os scaphoideum).

The scaphoid is one of the eight or nine principal bones forming part of the wrist in humans. The wrist is a very complicated joint since it consists, not of two bones rubbing against one another, but of eight or nine principal bones of unusual shapes held and moving in equilibrium under control of a highly developed system of ligaments. The scaphoid is of particular importance clinically because it is the wrist bone which tends most often to be fractured.

The scaphoid is the largest of the bones located in the first row of wrist bones (known as the first carpal row or proximal carpal row). The other principal bones in the proximal carpal row are the lunate, triangular and pisiform bones. The bones of the proximal row are articulated to the radius (of the forearm) and the articular disk. The second carpal row (also known as distal row) contains the trapezium or greater multangular, the trapezoid or lesser multangular, the capitate and the hamate. The bones of this second carpal row are firmly attached to the metacarpal bones of the hand.

The scaphoid is surrounded by the trapezium, trapezoid, capitate, lunate and radius, as illustrated in FIG. 1 (which illustrates the bone of the right hand viewed looking towards the palm). The scaphoid is "articulated" at the proximal side with the radius and at the distal side with the trapezium and trapezoid. Fractures of the scaphoid tend to occur, in around 70% of cases, in the central third thereof, as illustrated by the shaded area F in FIG. 1. If the fracture is not properly treated then a pseudathrosis or necrosis of the proximal bone fragment can occur. This is because, in a third of cases, blood supply to the scaphoid is furnished only by vessels at the distal side. Other ailments too, besides fractures, can lead to damage to or degeneration of the scaphoid.

U.S. Pat. No. 4,936,860 discloses a metal scaphoid prosthesis having a ledge engaging the trapezium and a bore receiving a suture to fix the prosthesis to the tendon slip or the palmar ligaments. Such attaching means aim to stabilize the prosthesis in the patient wrist, i.e. to force the prosthesis to return to its original position after a movement effected by the patient. This prosthesis has the drawback that complicate operations have to be carried out in order to appropriately fix it to the neighboring bones and ligaments. Furthermore, the material used to manufacture the prosthesis, namely vitallium, could wear away bones during movements made by the patient, as explained below.

It is not actually straightforward to determine the appropriate combination of shape, size and material enabling a suitable prosthesis to be produced for use in treating ailments of a joint or a bone. For example, the present inventors have found that there are disadvantages involved in the use of certain materials, known in the field of prostheses, such as polyethylene, ceramic zircon, titanium and vitallium.

In the case of polyethylene, the prosthesis is too soft, i.e. its modulus of elasticity, also called Young's modulus, which is of the order of 1 GPa (Giga Pascal), is far too low compared with that of bone, the latter being comprised within the range of 15 to 25 GPa. Such a prosthesis is therefore subject to deformation and becomes crushed after a relatively short period of use. Wear debris resulting from deterioration of the prosthesis can then migrate in some areas of the patient's wrist, which can cause painful inflammatory reactions for the patient.

In the case of zircon, titanium and vitallium, the prosthesis is too hard, so that it does not deform enough upon motions of the wrist, causing the bones in contact with the prosthesis to be stressed by the latter. Because of bad distribution of stresses, the patient experiences discomfort, for example, when pressing a fist down onto a surface. Also, there is a significant risk of wearing out the cartilage or bony surfaces in contact with the prosthesis due to the hardness of the prosthesis material.

OBJECTS AND SUMMARY OF THE INVENTION

It is an object of the present invention to provide an implant or prosthesis which resists wear and does not wear out the bones in contact with the prosthesis.

To this end, there is provided an implant having at least one contact surface portion designed to be in mobile contact with at least one bony surface when said implant is implanted in a patient, wherein said at least one contact surface portion is made of a material comprising pyrolytic carbon.

By "mobile contact", it is meant that the at least one contact surface portion of the implant may rub, slide or roll on the at least one bony surface of the patient.

Thus, the implant according to the invention uses pyrolytic carbon to form a contact surface which will be mobile with respect to the neighboring bone(s). Pyrolytic carbon is known in the art for its property of biocompatibility. It is already used in the manufacture of prostheses intended to be fixed to a bone. In such prostheses, the pyrolytic carbon surface in contact with the bone is generally porous, in order to allow the bone to fill the pores and, in this manner, to reinforce its join with the prosthesis.

Unlike known prostheses, the implant according to the present invention uses pyrolytic carbon to rub against neighboring bones, and not to form a joining surface. The present inventors have discovered that pyrolytic carbon exhibits a good coefficient of friction with bone, so that neither the implant nor the bones with which it is in contact are worn away during movements made by the patient. The implant may thus roll or slide on neighboring bones without entailing damage. Furthermore, the use of pyrolytic carbon improves the stability of the implant, by allowing a smoother fit between the implant and the bones, so that there is little chance that the implant be ejected from its housing during movement by the patient.

A main reason why pyrolytic carbon behaves well in its function of rubbing with the bones, resides in the fact that this material exhibits a modulus of elasticity, also called Young's modulus, approximately between 10 and 35 GPa, which is a substantially similar range to that of bone. Thus, when the implant presses against neighboring bones, and vice-versa, the respective stresses received by the implant and the bones equal each other out. The bones therefore receive stresses of the same order as those intended by nature. If the implant was, to the contrary, made from a material harder than bone, it would be likely to wear away or even perforate the neighboring bones. A too soft material would change the nature of the neighboring bones, making them loose their substance by decalcification. The bones would in this case wear away very quickly.

Accordingly, although pyrolytic carbon is the preferred material for manufacturing the implant according to the invention, other biocompatible materials could be used in the place of pyrolytic carbon, provided that their modulus of elasticity is approximately between 10 and 35 GPa.

According to another particularly advantageous feature of the invention, the external surface of the implant is polished in order to reduce even more the coefficient of friction. The external surface is preferably essentially made of pyrolytic carbon. Alternatively, the whole implant is made of pyrolytic carbon.

It is another object of the present invention to provide an implant or prosthesis which may be implanted into a patient more easily than the known implants.

To this end, the implant according to the invention is free from any attaching means, so that said implant remains free with respect to the neighboring bony surfaces when implanted in the patient.

The present inventors have discovered that it is possible, by virtue of the use of a material having a Young's modulus approximately comprised between 10 and 35 GPa, to produce an implant which remains stable in the patient and does not entail any or much wearing away, without it being necessary to provide attaching means to attach the implant against a bone or a ligament. Once introduced into the patient, the implant remains substantially mobile in its housing between neighboring bony surfaces. This implies greater comfort for the patient, since by leaving the implant free with respect to the bony surfaces, the patient is permitted a greater degree of liberty of movement.

If the natural housing between the bony surfaces is not adapted to the shape and movements of the implant, the implant's housing is prepared in advance by trimming one or several of the bony surfaces in an appropriate manner.

The implant according to the invention can be given a simple shape, since, on one hand, no attaching means is provided on its external surface, and, on the other hand, the housing into which it is to be introduced is prepared in advance so that its shape is adapted to the shape and movements of the implant.

The implant according to the present invention may be used notably as a joint between two bones or as a prosthesis intended to replace a bone or a part of a bone.

Thus, for example, when a joint between two bones has become painful, the facing bony surfaces, or only one of them, are trimmed to create a housing for the implant. The implant is then placed in its housing, to act as an interposition and joint piece between the two bones.

In the case where the implant according to the invention is used as a prosthesis, the defected part of the bone is removed, then a housing whose shape is adapted to the shape and movements of the implant is prepared by trimming one or several bones adjacent to the bone or the part of bone to be replaced. The implant is then introduced into the housing without being attached in order to restore the functionality of the defected bone.

BRIEF DESCRIPTION OF THE DRAWINGS

FIG. 2 shows an implant according to a first embodiment of the present invention, wherein

FIGS. 3 to 7 are diagrams serving to illustrate an explanation of the derivation of the shape of the implants according to the present invention, wherein:

FIG. 3 is a diagram schematically representing the movement of bones in the wrist by a simple model consisting of three solids;

FIG. 4 is a diagram illustrating how, at the points of contact between the solids of the simple model of FIG. 3, the shapes of the solids can be approximated by circles;

FIG. 5 is a diagram illustrating a system of inner contact which can also be used to approximate the movement of the intermediate solid of the model of FIG. 3 relative to the fixed solid;

FIG. 6 is a diagram illustrating a system of inner contact which can also be used to approximate the movement of the upper solid of the model of FIG. 3 relative to the intermediate solid;

FIG. 7 is a diagram illustrating how the shape of the implants according to the present invention can be derived from the approximations of FIGS. 5 and 6;

DETAILED DESCRIPTION OF THE PREFERRED EMBODIMENTS

A first embodiment of implant according to the present invention will now be described with reference to FIGS. 2 to 9. The implant according to this first embodiment is preferably used as a partial scaphoid implant.

The implant 1 is an element preferably made of pyrolytic carbon and graphite, and having a particular shape. More specifically, the pyrolytic carbon is deposited on a graphite substrate in a conventional manner, so as to fully coat the graphite substrate and constitute the external surface of the implant. Pyrolytic carbon is an isotropic ceramic manufactured at temperatures of around 1400° C. The compatibility of pyrolytic carbon with tissues and blood has been demonstrated by its use, for over 20 years, for making replacement cardiac valves (over 1 million of such valves have been implanted). The techniques for fabrication of elements in pyrolytic carbon and graphite are well-known and so will not be described in detail here. Details can be found, for example, in U.S. Pat. No. 3,526,005.

Because of its turbostratic structure, pyrolytic carbon, even coated on a graphite element, presents a high resistance to fracture with a low modulus of elasticity (Young's modulus), of about 20 to 35 GPa, and a significant elongation before rupture. Also, the use of pyrolytic carbon enables the bones which are in contact with the prosthesis not to be worn out by rubbing with the latter.

The external surface of the implant 1 is polished, thereby reducing friction between the implant 1 and the neighboring cartilage and/or bone, and does not comprise any attaching means. The surface roughness Ra. is at most 0.1 $\mu$m and preferably 0.02 $\mu$m.

In order to render the implant radio-opaque, i.e. to permit monitoring of the implant 1 by radiography once the implant has been implanted into the patient's wrist, the graphite can advantageously be impregnated with tungsten.

In variant, the implant 1 is made of massive pyrolytic carbon, in which case no graphite is present in the implant.

In another variant, the implant 1 is realized by coating a substrate, such as a graphite substrate, with a diamond-like carbon using a plasma-assisted PVD (Physical Vapor Deposition) or a plasma-assisted CVD (Chemical Vapor Deposition).

In another variant, the implant 1 is realized by coating a graphite substrate with an appropriate bio-compatible plastic. Such a bio-compatible plastic is for example parylene.

Figure 1:
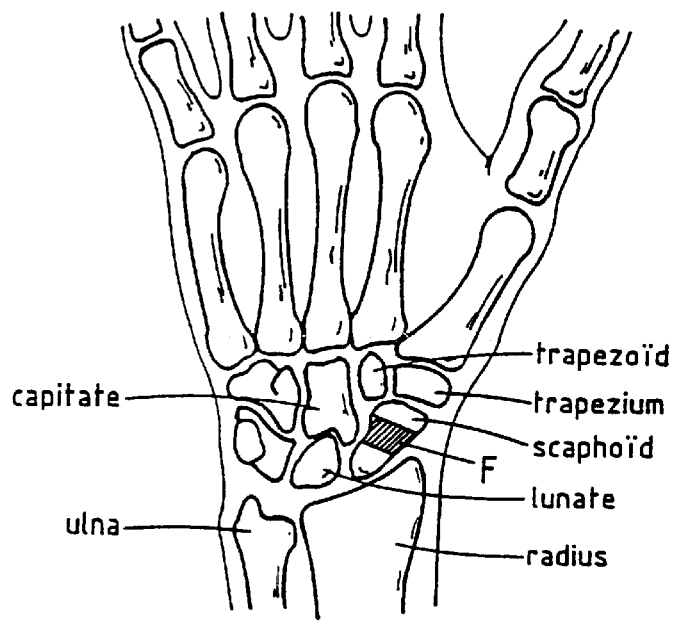
FIG. 1 is a diagram illustrating the principal bones of the human wrist (right hand, viewed looking at the palm)
Figure 2A:
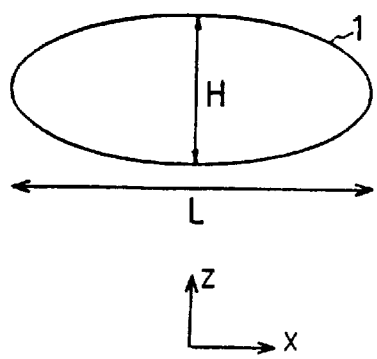
FIG. 2a is a side view.
Figure 2B:
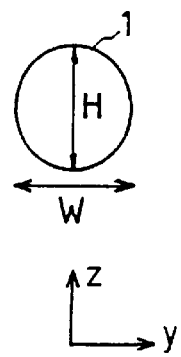
FIG. 2b is an end view of the implant.
Figure 2C:
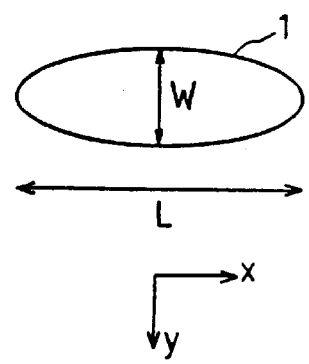
FIG. 2c is a top plan view of the implant.

The prosthesis 1 according to the first embodiment of the present invention is generally oval in cross-section in each one of three mutually perpendicular planes respectively designated by (x, z), (y, z) and (x, y) in FIGS. 2A, 2B and 2C. Moreover, the length L, height H, and width W of the prosthesis are all different from one another. Preferably, the prosthesis has a substantially ellipsoidal shape, and in particular is approximately elliptic in cross-sectional shape in each of the planes (x, z), (y, z) and (x, y), that is, the cross-sectional shape in a given plane corresponds to the shape delimited by a pair of facing, intersecting arcs having the same radius of curvature, with the points of intersection of the arcs being rounded off. The appropriate values of the radii of curvature are related to the anatomy of the wrist, as is explained in greater detail below.

A statistical study of fractures of the scaphoid, conducted on both male and female patients, has enabled the determination of a set of "standard" prostheses according to the invention, suitable for treating the vast majority of ailments of the scaphoid. The dimensions of these "standard" prostheses are given in Table 1 below.

TABLE 1

|  | Length L (mm) | Width W (mm) | Height H (mm) |
| --- | --- | --- | --- |
| Example 1 | 18.9 | 9.5 | 10.6 |
| Example 2 | 17.9 | 8.5 | 9.6 |
| Example 3 | 17 | 7.5 | 8.6 |

Figure 8:
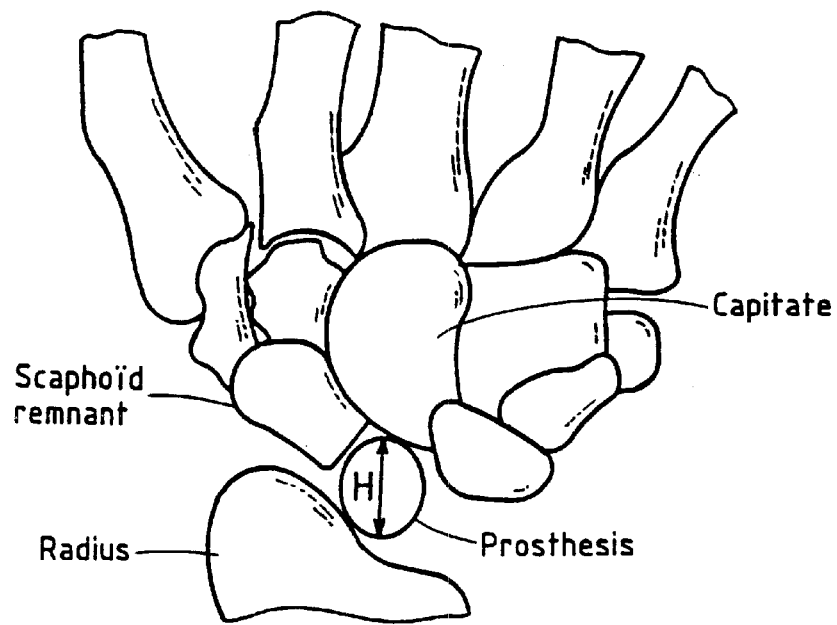
FIG. 8 is a diagram illustrating the orientation of a prosthesis according to the first embodiment of the present invention when implanted in a wrist (viewed looking at the back of a right hand)
Figure 9:
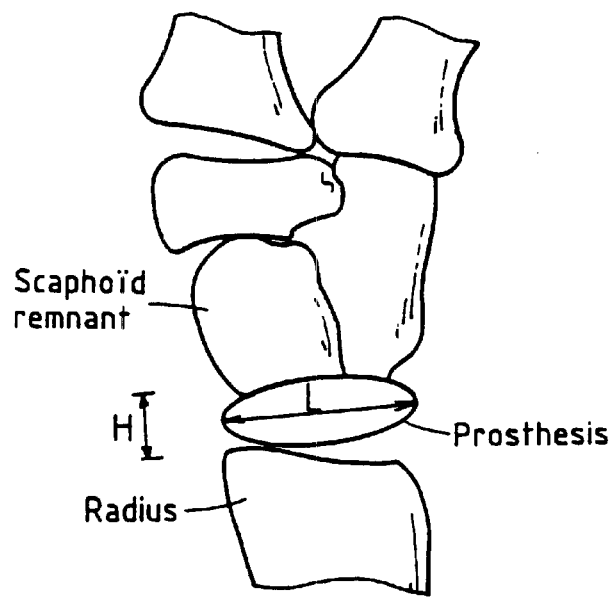
FIG. 9 is a diagram illustrating the orientation of a prosthesis according to the present invention when implanted in a wrist (viewed looking at the side of a right hand, the thumb facing forwards)

As mentioned above, the implant 1 is substantially ellipsoidal and has a first portion of large radius of curvature (relatively flat) which corresponds to the profile of the scaphoid facing the radius (see FIG. 9). It also has a second portion of small radius of curvature (relatively highly curved) which corresponds to the profile of the scaphoid between the head of the capitate and the radius (see FIG. 8). The width W of the implant 1 being smaller than the height H, leads to an increase in the curvature of the second portion and, thus, to an increase in ease of rolling of the prosthesis relative to the capitate and radius. Moreover, it has been found that the risk of dislocation of the wrist joint after implantation of the prosthesis is significantly reduced when W≠H.

The shape of the implant according to the present invention was derived from a consideration of the kinematics of the bones in the wrist, based on certain models and approximations described below with reference to the diagrams of FIGS. 3 to 7.

Figure 3:
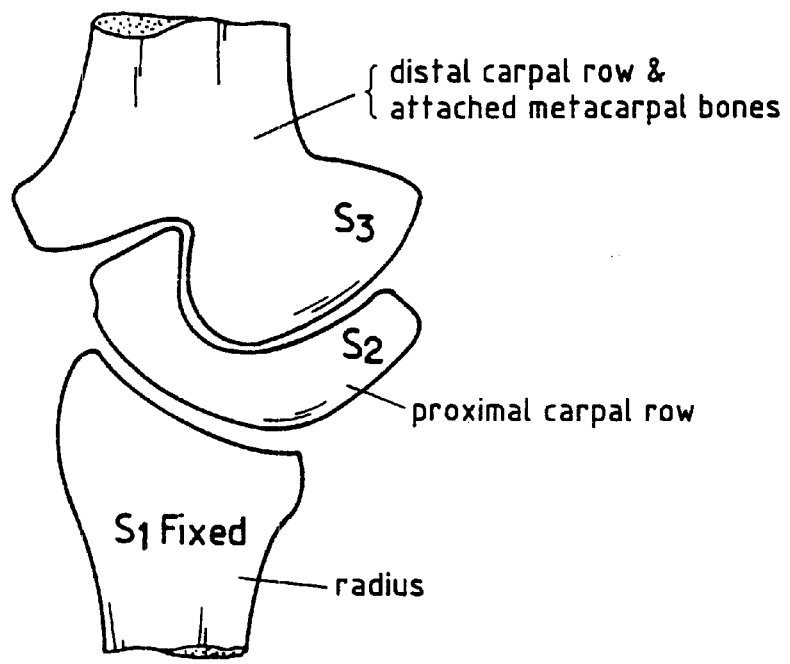

Movements of the wrist can be analyzed using a model treating the wrist as being composed of three solids S1, S2 and S3, roughly as illustrated in FIG. 3. The solid S1 corresponds to the radius and, thus, is considered to be fixed. The solid S2 corresponds to the bones of the first carpal row (scaphoid, lunate, triangular and pisiform bones), treated as a single entity. The solid S3 corresponds to the bones of the second carpal row (trapezium, trapezoid, capitate and hamate) treated as a single entity. Movements of the third solid S3 are considered to be caused by movements of the intermediate second solid S2, that is:

Displacement (S3 relative to S1)=Displacement (S2 relative to S1)+Displacement (S3 relative to S2).

The movements of the wrist are such that the three solids of the model of FIG. 3 experience only small displacements relative to one another. It thus becomes possible to reduce the analysis of movements of the wrist to an analysis of what happens at the points of contact between the different solids of the model of FIG. 3. At these points of contact, I, the shapes of the respective solids can be approximated using circles, as illustrated in FIG. 4.

Figure 4:
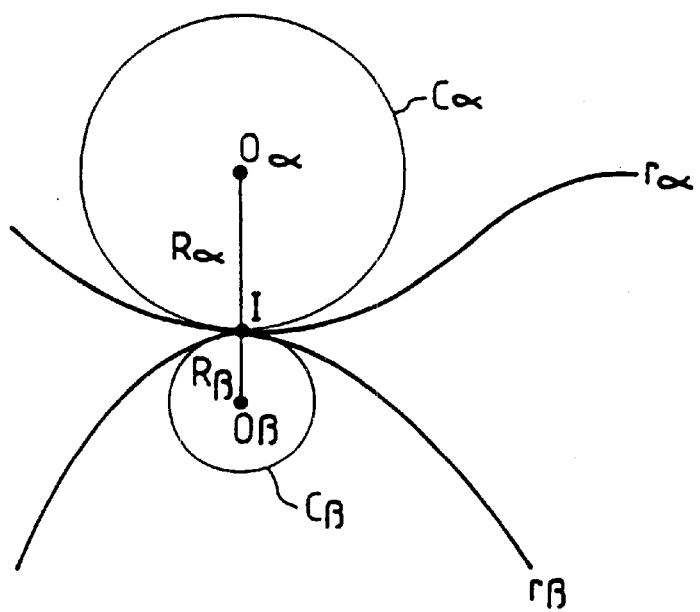

In FIG. 4, the curves $\Gamma_\alpha$ and $\Gamma_\beta$ represent the curved surfaces of solids which are in contact at a point I. At the point of contact, these surfaces can be represented by respective circles $C_\alpha$ and $C_\beta$, having centers $O_{60}$ and $O_\beta$ and radii $R_\alpha$ and $R_\beta$.

Figure 5:
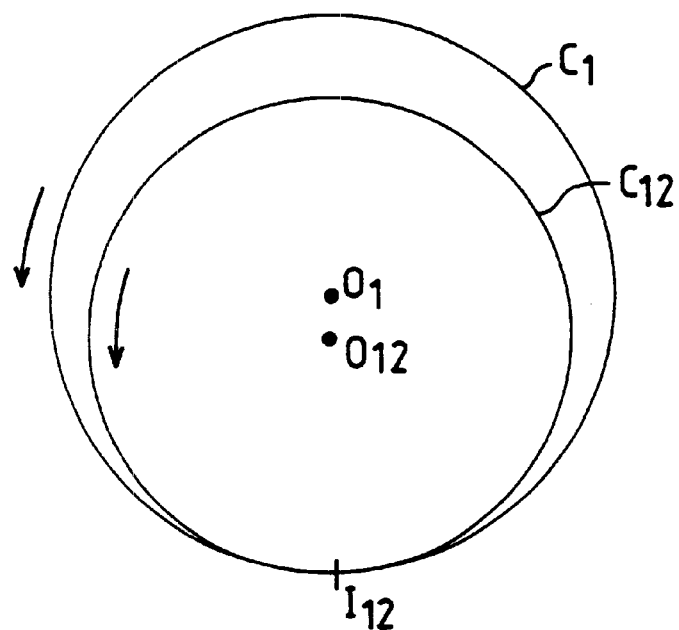

The movement of the intermediate solid S2 relative to the fixed solid S1 can, thus, be represented, as in FIG. 5, by a pair of nested circles C1 (representing the surface of the fixed solid S1 at the point of contact) and C12 (representing the portion of intermediate solid S2 at the point of contact with S1), the circle C12 rolling with respect to the circle C1.

Figure 6:
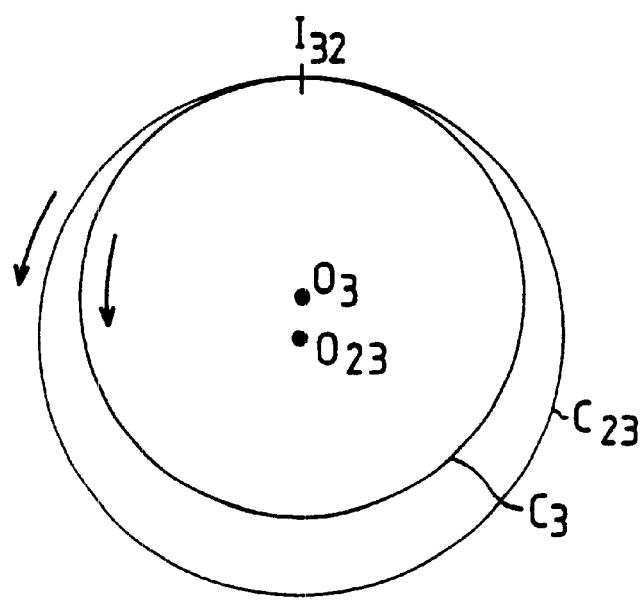

Now, when the wrist moves, the distal carpal row (modeled as solid S3) rotates in the same direction as the first carpal row (modeled as intermediate solid S2). In order for this to be possible, and for the angles of articulation between the various bones to be respected, it is necessary to consider that, on the model of FIG. 3, the solid S3 forms with the solid S2 a system resembling a mechanical gear with inner contact, as illustrated in FIG. 6. In FIG. 6, the movement of the solid S3 relative to the intermediate solid S2 is represented by a pair of nested circles C3 (representing the surface of solid S3 at the point of contact) and C23 (representing the portion of the intermediate solid S2 at the point of contact with S3), the circle C23 rolling with respect to the circle C23. This type of dynamic system results in rolling contact without slipping.

In order for the transmission of movement to solid S3 to be as effective as possible, it is necessary that the instantaneous contact between the various solids should take the form of a point contact (that is, the surfaces remain as tangent to one another as possible), and that slipping should be avoided. Such a situation will arise when the surfaces in contact are conjugated surfaces.

Figure 7B:
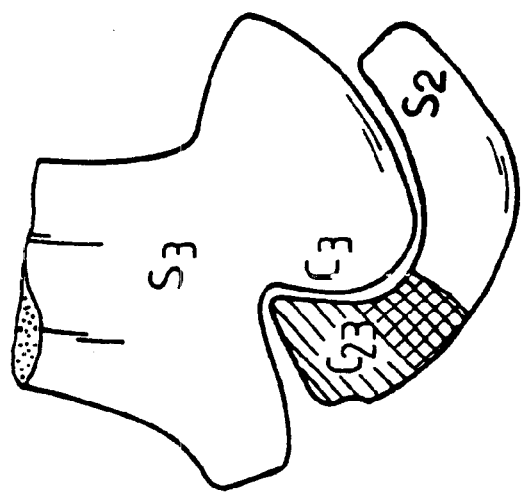
Figure 7A:
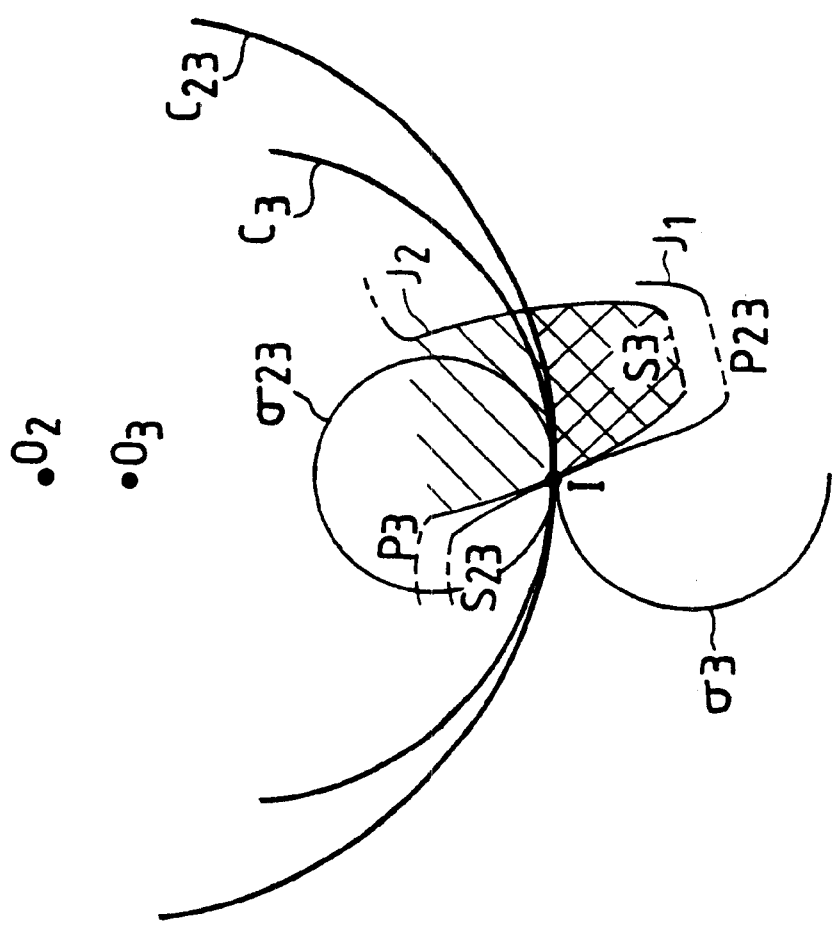

FIG. 7 shows the shape of conjugated surfaces $J_1$, $J_2$ in a gear having internal contact and illustrates the analogy between the teeth of such a gear and that portion of the solid S2 which corresponds to the scaphoid. It can be considered that the hatched portions of the gear tooth and the solid S2 correspond to the scaphoid. The prosthesis of the first embodiment of the present invention is designed to replace that portion of the scaphoid indicated by the cross-hatched portion of the solid S2. In practice, the surface of the radius facing this portion of the scaphoid is not smooth but bowed inwards, such that the prosthesis according to the invention can be considered to correspond to the extremity of the tooth represented by the surface $J_2$.

Accordingly, the prosthesis of the present invention is designed to have a portion having a large radius of curvature (i.e. a flatter portion) corresponding to the conjugated profile of the scaphoid facing the radius and, for similar reasons, to have a portion having a small radius of curvature (i.e. a highly-curved portion) corresponding to the conjugated profile of the scaphoid between the head of the capitate and the radius.

A preferred method of treating ailments of the scaphoid according to the present invention will now be described.

The preferred method of treatment consists in the surgical removal of a proximal scaphoid portion and the replacement thereof by an implant of the type described above. Before surgery, x-rays of the wrist are taken in order to determine the appropriate dimensions of the implant. More particularly, postero-anterior and lateral wrist x-rays are taken in order to evaluate the amount of piston motion required and the volume to be filled, the choice of implant dimensions being determined by the result of the evaluation, for example using overheads being of the same scale as the X-ray pictures and showing the outside profile of the prosthesis. The surgical procedure is then, as follows:

The approach is made dorsally, creating a Z-shaped incision in the skin along the extensor carpi radialis brevis and curving towards the thumb base in a proximo-distal fashion. Afterwards, the procedure uses a way between the radialis tendons or on the ulnar side of extensor carpiradialis brevis. (The extensor pollicis longus is repaired and retracted because otherwise it interferes with this operation).

The capsule is incised longitudinally up to the capitate. It should be subperiosteum pushed towards the radial and ulnar sides on the lip of the radius.

The scaphoid fragment is removed, after sectioning the scapho-lunate ligament and excising the fibrous sinovium if necessary. If needed, an osteomy can be performed, in an oblique way, radial to ulnar side, on the retained distal scaphoid fragment. It has been found in some cases that the radial styloidprocess can be removed without compromising in any way the stability of the implant. The capitate is not shaped but left convex. If the scaphoid surface of the distal radius has arthrosic signs then it is appropriate to create Pridies perforations on the radial fossa using a 1/10 broach.

At this stage, the prosthesis of chosen dimensions can be put into place. As indicated above, the portion of the implant having a small radius of curvature (i.e. a highly-curved portion) corresponding to the conjugated profile of the scaphoid between the head of the capitate and the radius is disposed facing those bones (see FIG. 8), whereas the portion of the implant having a large radius of curvature (i.e. a flatter portion) corresponding to the profile of the scaphoid facing the radius is disposed facing the upper side of the radius (the radius being oriented as shown in FIG. 9). The prosthesis is merely positioned in its housing between the remaining distal portion of the scaphoid, the radius, the capitate and the lunate, without being fixed.

FIGS. 8 and 9 illustrate the disposition of the prosthesis in the wrist of a right hand. FIG. 8 represents a view looking at the back of a right hand and FIG. 9 represents a view looking at the side of the right hand, the thumb facing forwards.

Preferably, the stability of implant positioning under movements of flexion-extension and lateral bending of the wrist is checked, even while the capsule is still open.

As a matter of routine, the capsular closure is loose, performed longitudinally using two or three points in X. The extensor radialis tendons will reposition on the capsular opening and especially stabilize the dorsal gap in flexion and in a dynamic way. The extensor retinaculum incised or excised distally is not reconstituted.

The skin closure is done on a suction drain. The day after the surgical procedure has been performed, the wrist should be immobilized in a neutral position in a short arm cast. This cast should be left in place for two to three weeks. After this time, the rehabilitation can start using a removable splint. This splint is to be worn in an intermittent fashion for about one month. Use of a removable splint (no arm cast) can sometimes lead to early rehabilitation. However, no acceleration of the recovery process is seen and mobility results are identical.

As an alternative embodiment of the method according to the invention, the choice of the dimensions of the prosthesis to be implanted into the patient's wrist is performed using color coded sizers having the same shape as that of the implant 1. Each color coded sizer consists of an element having a particular size and a corresponding color. Several color-coded sizers are successively inserted into the patient wrist. The particular size of the color coded sizer that is best adapted to the patient's wrist corresponds to the size of the prosthesis to be implanted.

It should be noted that the above-described method of treatment is contra-indicated in certain cases, notably in cases of infection or systemic disease, advanced deformity of the distal portion of the radius, SLAC wrist, advanced silicone synovitis of the wrist bone, irreparable conditions of the tendon system or inadequate soft tissue support.

FIGS. 10 to 16 show implants according to second to eighth embodiments of the present invention. FIGS. 17 to 22 show various applications for the second to eighth embodiments. The plane sections represented in FIGS. 10 to 16 are each obtained by intersecting the implant with a plane (x,z), (x,y) or (y,z) passing through its geometric center. The three planes (x,z), (x,y) and (y,z) which will be referred to below are mutually perpendicular.

Figure 10A:
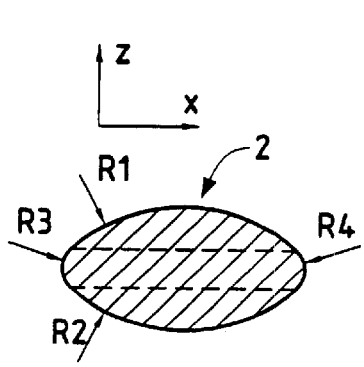
FIGS. 10A and 10B show two perpendicular section views of an implant according to a second embodiment of the present invention.
Figure 10B:
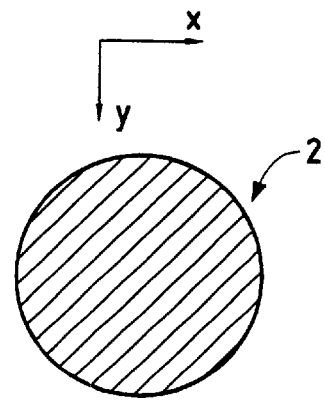

According to the second embodiment of the invention, illustrated in FIGS. 10A, 10B, the implant, denoted by reference numeral 2, exhibits an oval first plane section (FIG. 10A) and a second plane section, perpendicular to the first plane section, which takes the form of a disc (FIG. 10B). The contour of the oval plane section is composed of arcs of circles, and more specifically of a first pair of facing arcs of circles having respective radii of curvature R1 and R2, and a second pair of facing arcs of circles having respective radii of curvature R3 and R4, with R1 and R2 being greater than R3 and R4. In the example as shown in FIGS. 10A, 10B, the radii R1 and R2 are equal to each other, as well as radii R3 and R4.

Figure 11A:
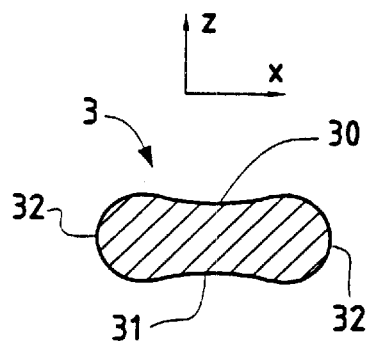
FIGS. 11A to 11C show three perpendicular section views of an implant according to a third embodiment of the present invention.
Figure 11B:
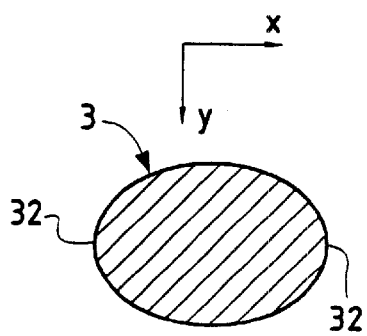
Figure 11C:
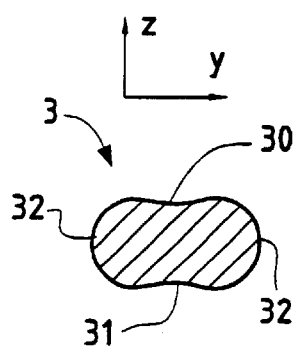

According to the third embodiment of the invention, illustrated in FIGS. 11A, 11B, 11C, the implant, denoted by reference numeral 3, has a first surface portion 30 whose intersection with each one of the perpendicular planes (x,z), (y,z) is concave, and a second surface portion 31, facing the first portion 30, whose intersection with each one of the perpendicular planes (x,z) and (y,z) is also concave. The implant 3 further comprises two lateral surface portions 32, preferably substantially curved, connecting the surface portions 30 and 31 to each other. In plane section in the plane (x,y), the implant 3 exhibits an oval or substantially elliptic shape. By "substantially elliptic", it is meant that this plane section may be elliptic, almost elliptic, circular or composed of arcs of circles.

Figure 12A:
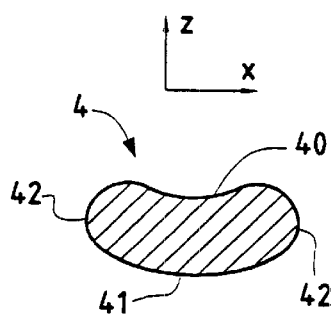
FIGS. 12A to 12C show three perpendicular section views of an implant according to a fourth embodiment of the present invention.
Figure 12B:
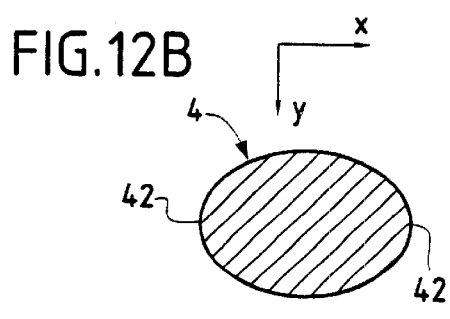
Figure 12C:
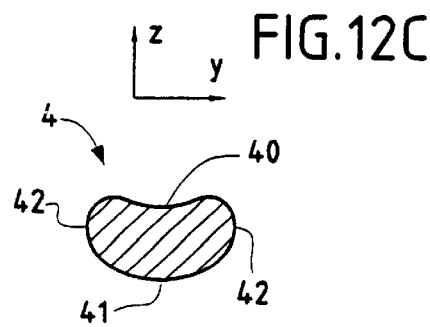

According to a fourth embodiment, illustrated in FIGS. 12A, 12B, 12C, the implant, denoted by reference numeral 4, has a first surface portion 40 whose intersection with each one of the perpendicular planes (x,z) and (y,z) is concave, and a second surface portion 41, facing the first surface portion 40, whose intersection with each one of the planes (x,z) and (y,z) is convex. The plane sections in the planes (x,z) and (y,z) thus are in the form of a bean or a crescent. The plane section in the plane (x,y) is oval or substantially elliptic. The implant 4 further comprises lateral surface portions 42, preferably substantially curved, connecting the surface portions 40 and 41 to each other.

Figure 13A:
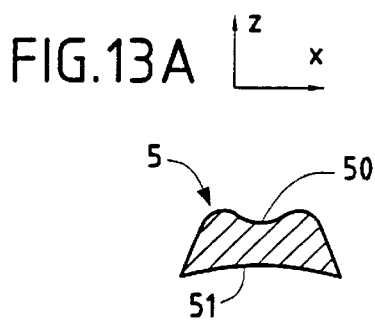
FIGS. 13A to 13C show three perpendicular section views of an implant according to a fifth embodiment of the present invention.
Figure 13B:
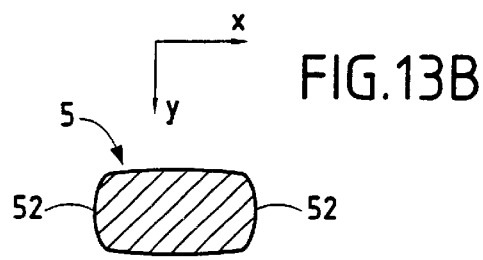
Figure 13C:
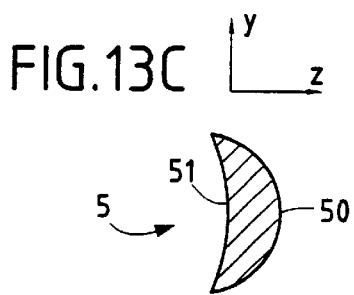

According to a fifth embodiment, illustrated in FIGS. 13A, 13B, 13C, the implant, denoted by reference numeral 5, has a surface portion 50 whose intersection with the plane (x,z) is concave and whose intersection with the plane (y,z) is convex. The implant 5 further comprises a surface portion 51, facing the surface portion 50, whose intersection with each one of the planes (x,z) and (y,z) is concave. In plane section in the plane (y,z), the implant 5 takes the form of a crescent (FIG. 5C). More specifically, the plane section of the implant 5 in the plane (y,z) exhibits a contour consisting of two contour portions, one of which, corresponding to the surface portion 50, is convex, and the other of which, corresponding to the surface portion 51, is concave. Each end of the convex contour portion joins a corresponding end of the contour concave portion. The plane section in the plane (x,y) is substantially rectangular, with slightly curved lateral edges 52 (FIG. 13B).

Figure 13D:
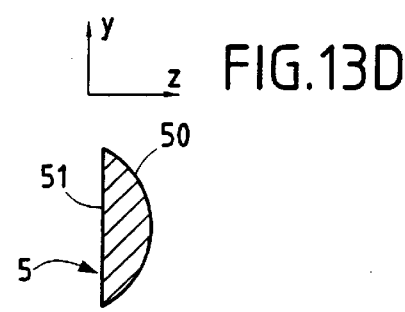

According to a simplified variant of the implant 5, the surface portion 51 has a straight plane section in the plane (y,z), as illustrated in FIG. 13D. In the variant of FIG. 13D, the plane section of the implant 5 in the plane (y,z) has a contour consisting of two contour portions, one of which, corresponding to the surface portion 50, is convex, the other of which, corresponding to the surface portion 51, is straight. Each end of the convex contour portion joins a corresponding end of the contour straight portion.

Figure 14A:
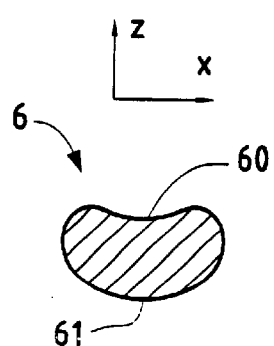
FIGS. 14A to 14C show three perpendicular section views of an implant according to a sixth embodiment of the present invention.
Figure 14B:
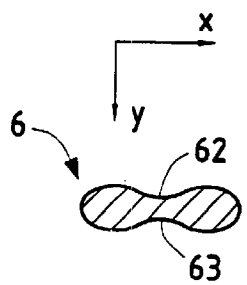
Figure 14C:
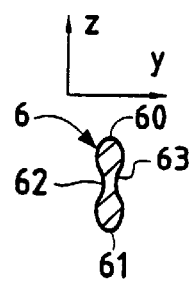

According to a sixth embodiment, illustrated in FIGS. 14A, 14B, 14C, the implant, denoted by reference numeral 6, has a surface portion 60, whose intersection with the plane (x,z) is concave and whose intersection with the plane (y,z) is convex, and a surface portion 61, facing the surface portion 60, whose intersection with each one of the planes (x,z) and (y,z) is convex. The implant 6 further comprises facing surface portions 62 and 63 connecting the surface portions 60 and 61 to each other. The surface portions 62, 63 each have a concave intersection with the planes (x,y) and (y,z). The surface portions 62, 63 have a greater size than the surface portions 60, 61, so that the implant 6 exhibits a flat shape in the planes (x,y) and (y,z).

Figure 15A:
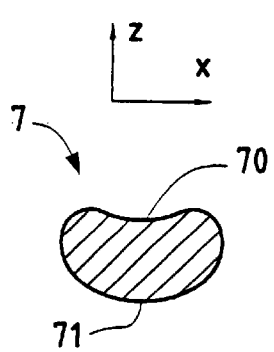
FIGS. 15A to 15C show three perpendicular section views of an implant according to a seventh embodiment of the present invention.
Figure 15B:
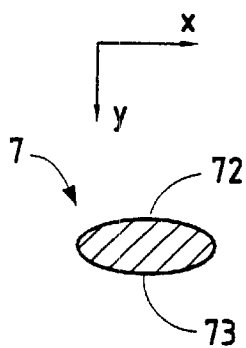
Figure 15C:
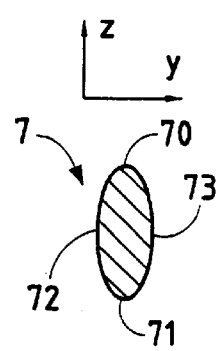

According to a seventh embodiment, illustrated in FIGS. 15A, 15B, 15C, the implant, denoted by reference numeral 7, has a surface portion 70, whose intersection with the plane (x,z) is concave and whose intersection with the plane (y,z) is convex, and a surface portion 71, facing the surface portion 70, whose intersection with each one of the planes (x,z) and (y,z) is convex. The implant 7 further comprises facing surface portions 72 and 73 connecting the surface portions 70 and 71 to each other. The surface portions 72, 73 each have a convex intersection with the planes (x,y) and (y,z). The surface portions 72, 73 have a greater size than the surface portions 70, 71, so that the implant 6 exhibits a flat shape in the planes (x,y) and (y,z).

Figure 16A:
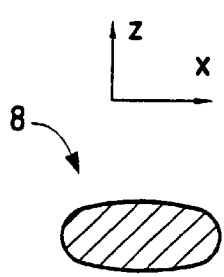
FIGS. 16A to 16C show three perpendicular section views of an implant according to an eighth embodiment of the present invention.
Figure 16B:
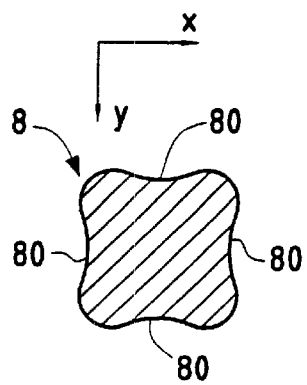
Figure 16C:
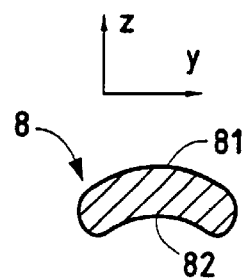

According to an eighth embodiment, illustrated in FIGS. 16A, 16B, 16C, the implant, denoted by reference numeral 8, has a substantially oval plane section in the plane (x,z), a substantially square or rectangular plane section in the plane (x,y), and a crescent-shaped plane section in the plane (y,z). The sides 80 of the substantially square section are slightly concave, as shown in FIG. 16B. The plane section in the plane (y,z) has a convex contour portion 81 facing a concave contour portion 82.

The implant 2 to 8 as described above are manufactured in the same manner as implant 1 shown in FIG. 2. Furthermore, like implant 1, implants 2 to 8 have an external surface which is entirely polished. The whole external surface of each one of implants 1 to 8 is smooth, continuous and regular, and does not comprise any attaching means.

FIGS. 17 to 22 show examples of applications for the implants 2 to 8 as described above.

Figure 17A:
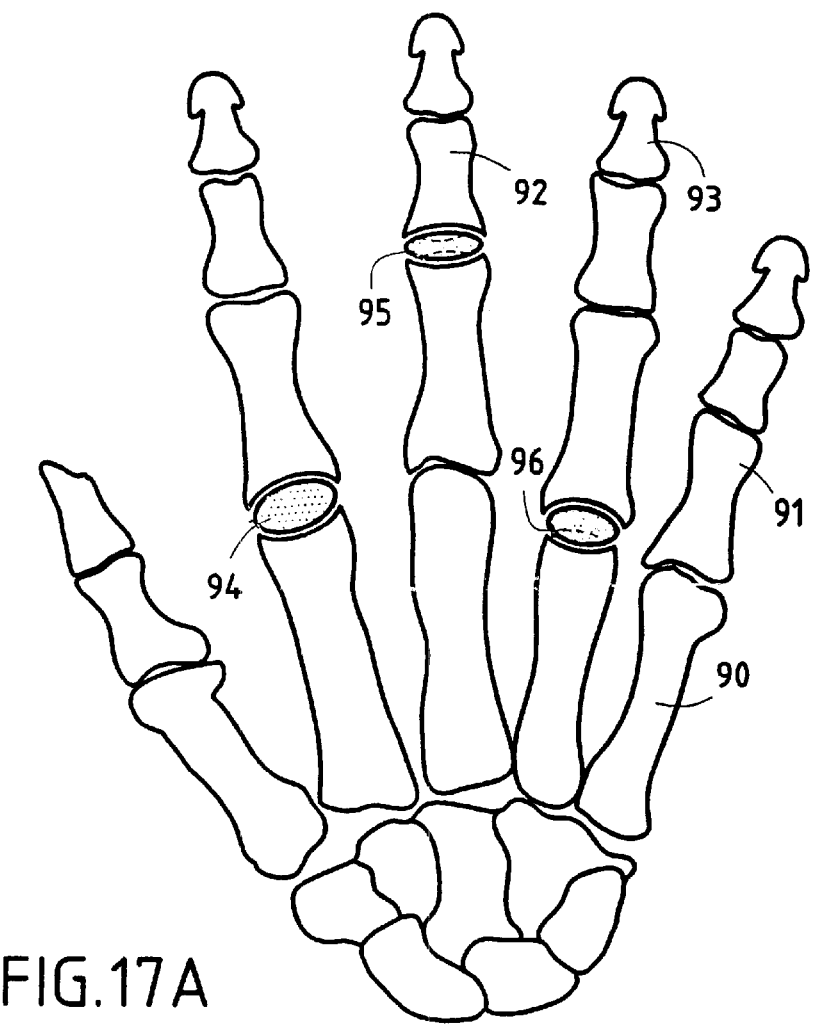
FIG. 17A is a schematic top view of a right hand having implants according to the invention.

FIG. 17A shows a top view of a right hand. The implants 1 to 4 as described above may each be implanted into a patient's finger to serve as a metacarpo-phalangeal joint, between a metacarpal bone 90 and a proximal phalanx 91, or as a interphalangeal joint, between a proximal phalanx 91 and a middle phalanx 92, or between a middle phalanx 92 and a distal phalanx 93.

Reference numeral 94 denotes an implant according to the invention, located between the metacarpal bone and the proximal phalanx of the index finger. The implant 94 is identical to the implant 1 or the implant 2 illustrated in FIGS. 2A to 2C and 10A, 10B. Reference numeral 95 denotes an implant according to the invention located between the proximal phalanx and the middle phalanx of the middle finger. The implant 95 is identical to the implant 3 illustrated in FIGS. 11A to 11C. Reference numeral 96 denotes an implant according to the invention, located between the metacarpal bone and the proximal phalanx of the ring finger. The implant 96 is identical to the implant 4 illustrated in FIGS. 12A to 12C.

Each one of the implants 94, 95, 96 is placed, without being attached, into a housing having an adapted form, which is prepared in advance before the introduction of the implant. Thus, the housing of the implant 94, between the metacarpal bone and the proximal phalanx of the index finger, exhibits a substantially ellipsoidal or rectangular shape, whilst the housing of the implant 95 has for example two facing concave faces and the housing of the implant 96 has for example a concave face and a convex face opposite each other.

Figure 17B:
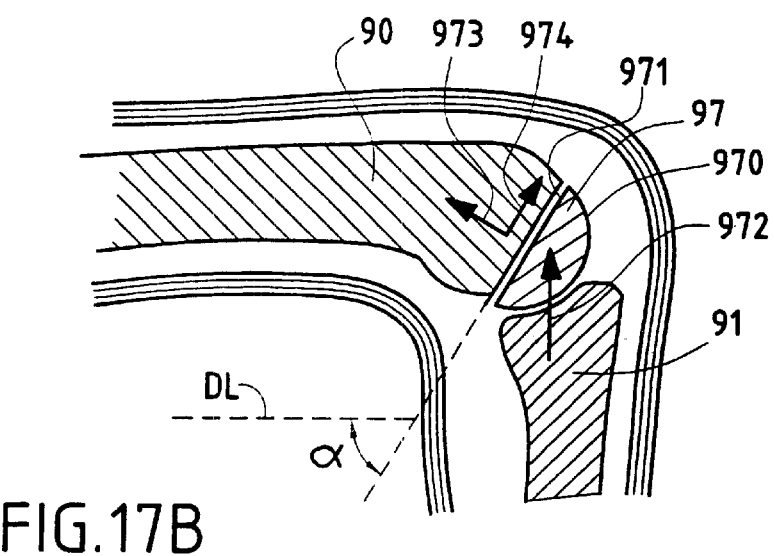
FIG. 17B shows a section view of an implant according to the invention implanted in a patient's finger.

FIG. 17B shows, in plane section, a metacarpo-phalangeal joint implant 97 located between the metacarpal bone 90 and the proximal phalanx 91 of a finger. In the configuration illustrated in FIG. 17B, the finger is in flexion. The implant 97 is of the type of the implant 5 illustrated in FIGS. 13A to 13D, and comprises a surface 970, corresponding to the surface 50 shown in FIGS. 13A to 13D, facing the phalanx 91 and a surface 971, corresponding to the surface 51, facing the metacarpal bone 90. By virtue of the shape of implant 97, a part of the stresses applied by the phalanx 91 on the implant 97 in the direction of arrow 972 is transmitted to the metacarpal bone 90, as indicated by arrow 973, by the fact that the implant 97 presses on the metacarpal bone 90, whilst another part (arrow 974) is absorbed by the neighboring ligaments and tendons. Thus, the shape of the implant 97 makes it possible to avoid the ejection of the implant from its housing. The implant's housing 97 is obtained by removing an end portion of the metacarpal bone 90 in such a manner that the surface of the resulting end be oriented according to an angle a with respect to a longitudinal direction DL of the metacarpal bone 90.

Figure 18A:
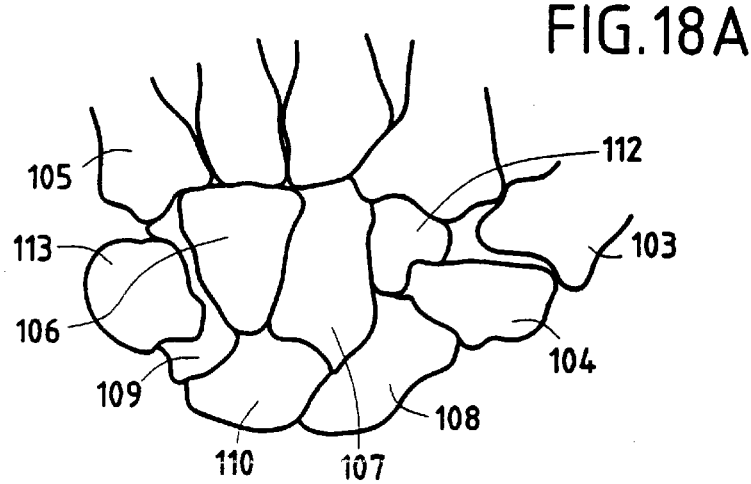
FIG. 18A is a schematic top view of a left wrist.
Figure 18B:
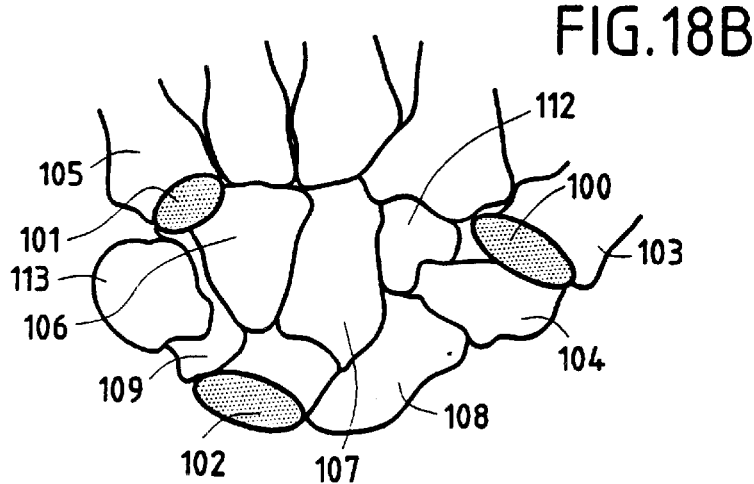
FIGS. 18B and 18C are schematic top views of a left wrist having implants according to the invention.

FIG. 18A is a top view of a left wrist, and FIG. 18B shows the same left wrist into which implants 100, 101 and 102 according to the invention have been introduced. The implant 100 is used as a trapezio-metacarpal joint. This implant is placed in a housing obtained by trimming the opposite surfaces of the metacarpal bone 103 of the thumb and the trapezium 104. The implant 101 is used as a carpo-metacarpal joint between notably the metacarpal bone 105 of the ring finger and the hamate bone 106. The implant 102 is used as a total radio-carpal joint or as a part of a radio-carpal joint between the radius (not shown) and the capitate 107, and is in contact with the scaphoid 108 and the triquetrum 109, in order to play the role of the key stone of the wrist instead of the lunate 110. FIG. 18B shows an implant 102 forming a part of a radio-carpal joint. The implants 100, 101 and 102 are preferably identical to the implant 1 or the implant 2 illustrated in FIGS. 2A to 2C and 10A, 10B.

Figure 18C:
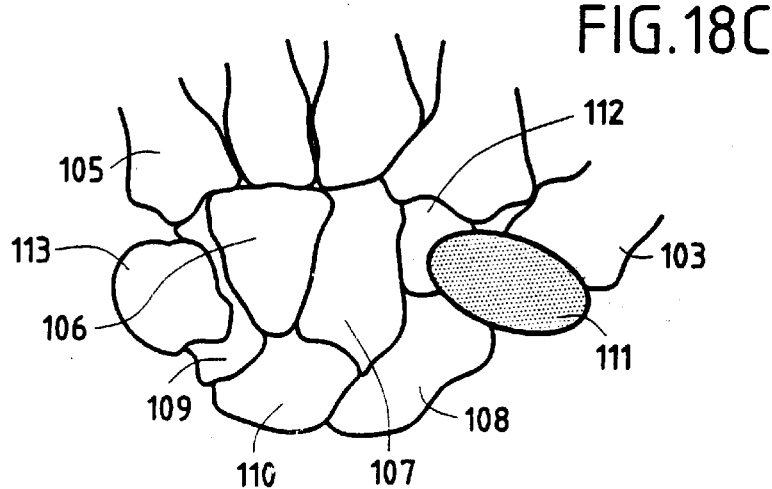

FIG. 18C shows a trapezium prosthesis 111 implanted in the left wrist of FIG. 18A. The housing of the prosthesis 111 is prepared by removing the trapezium 104 and by slightly trimming the surface of the metacarpal bone 103 facing the trapezium 104. The prosthesis 111 is also identical to implant 1 or 2.

Figures 19A, 19B:
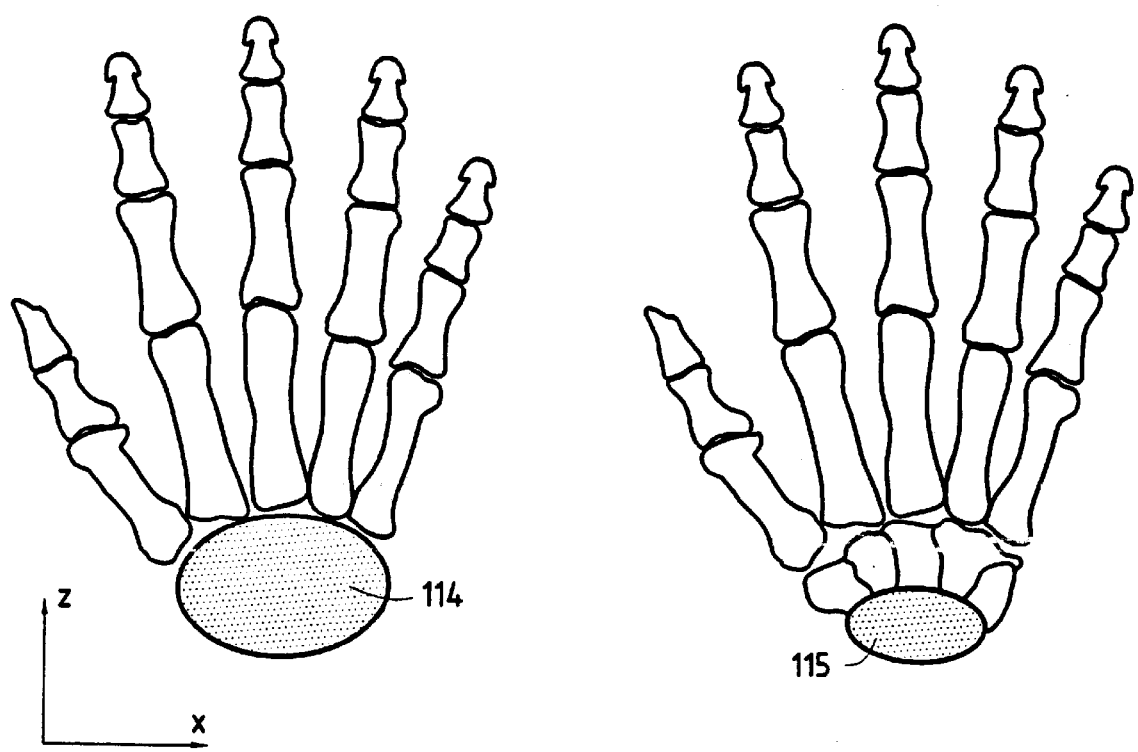
FIG. 19A is a schematic top view of a right hand into which an overall wrist prosthesis according to the invention has been introduced.
FIG. 19B is a schematic top view of a right hand into which a partial wrist prosthesis according to the invention has been introduced.

FIG. 19A shows a total wrist prosthesis 114 according to the invention, of the type of implant 1 or 2, replacing all the wrist's bones, namely the trapezium 104, the trapezoid 112, the scaphoid 108, the lunate 110, the triquetrum 109, the pisiform bone 113, the capitate 107 and the hamate bone 106. FIG. 19B shows a partial wrist prosthesis according to the invention, replacing the first carpal row, namely the scaphoid 108, the triquetrum 109 and the lunate 110.

Figure 20:
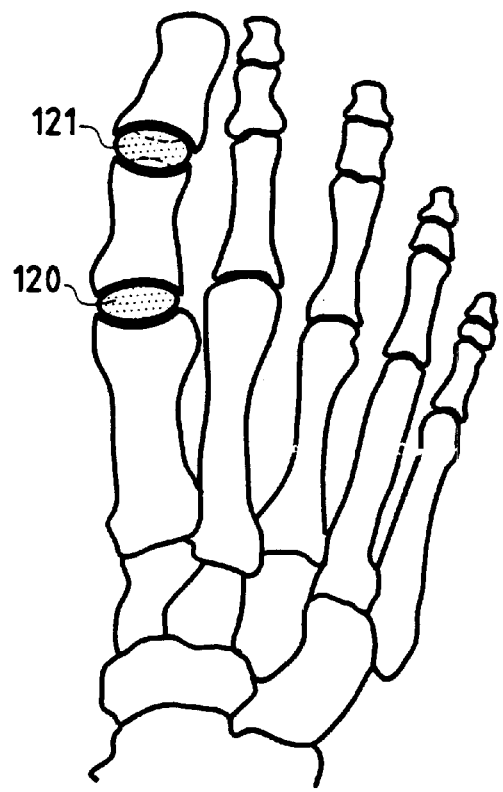
FIG. 20 is a schematic top view of a right foot into which implants according to the invention have been introduced.

FIG. 20 is a top view of a right foot having a metatarso-phalangeal joint 120 and an interphalangeal joint 121, which may each consist of one of the implants 1 to 4 as previously described.

Figure 21:
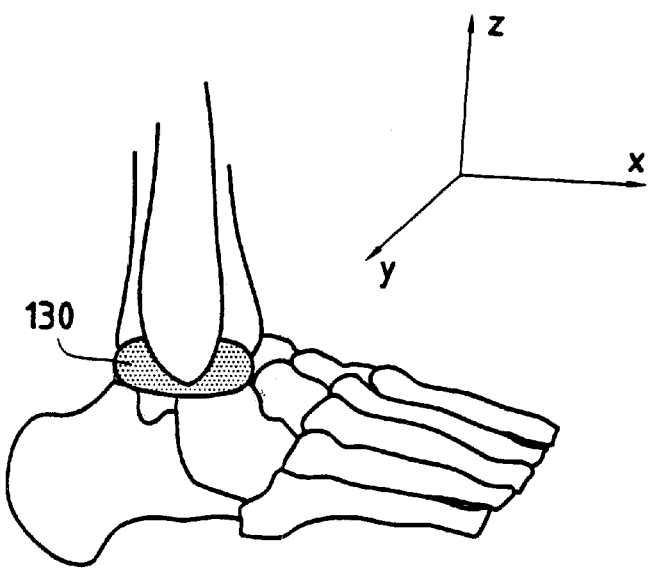
FIG. 21 is a schematic perspective view of an ankle prosthesis according to the invention implanted in a patient.

FIG. 21 shows an ankle prosthesis 130 according to the invention, implanted in a patient, without being fixed, in replacement of the astragalus. The prosthesis 130 is preferably identical to the implant 8 illustrated in FIGS. 16A to 16C, but may also consist of one of the implants 1 and 2 shown in FIGS. 2A to 2C and 10A to 10C.

Figure 22:
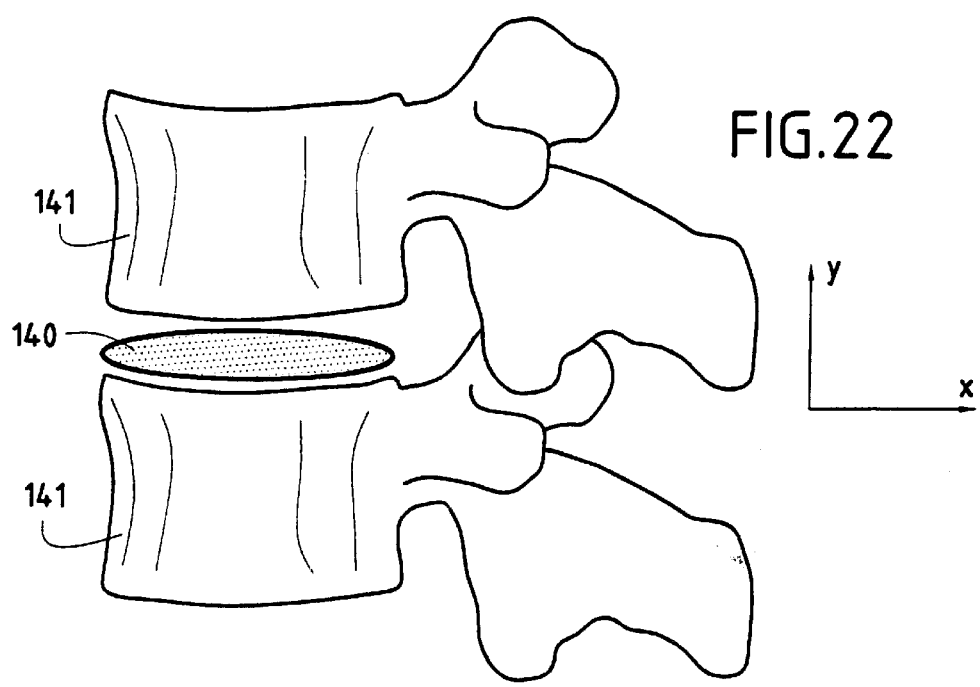
FIG. 22 is a schematic side view of an intervertebral disc according to the invention implanted in a patient.

FIG. 22 is a side view of an intervertebral disc prosthesis 140 according to the invention, located between two vertebrae 141. The prosthesis 140 is identical to the implant 6 illustrated in FIGS. 14A to 14C or to the implant 7 illustrated in FIGS. 15A to 15C.

What is claimed is:

1. An implant having at least one contact surface portion designed to be in direct mobile contact with at least one bony surface when said implant is implanted in a patient, wherein said at least one contact surface portion is made of a material comprising pyrolytic carbon, and wherein said implant is free from any attaching means, so that said implant remains free with respect to said patient's bones when implanted in said patient.

2. An implant according to claim 1, wherein said at least one contact surface portion is polished.

3. An implant according to claim 1, wherein said implant remains free with respect to said at least one bony surface when implanted in said patient.

4. An implant according to claim 3, having an external surface which is entirely polished.

5. An implant according to claim 3, wherein said pyrolytic carbon forms at least an external surface of said implant.

6. An implant according to claim 1, having a substantially ellipsoidal shape.

7. An implant according to claim 1, having an oval first plane section and a second plane section, perpendicular to said first plane section, having the shape of a disc.

8. An implant according to claim 7, wherein said first plane section includes a contour consisting of arcs of circles.

9. An implant according to claim 1, comprising a first surface portion whose respective intersections with a first plane and a second plane, perpendicular to the first plane, are concave, and a second surface portion, opposite the first surface portion, whose respective intersections with the first and second planes are also concave.

10. An implant according to claim 9, further comprising a plane section, in a third plane perpendicular to the first and second planes, with a substantially elliptic shape.

11. An implant according to claim 1, comprising a first surface portion whose respective intersections with a first plane and a second plane, perpendicular to the first plane, are concave, and a second surface portion, opposite the first surface portion, whose respective intersections with the first and second planes are convex.

12. An implant according to claim 11, further comprising a plane section, in a third plane perpendicular to the first and second planes, with a substantially elliptic shape.

13. An implant according to claim 1, having a plane section with a contour consisting of a convex portion and a concave portion, wherein each end of the convex portion joins a corresponding end of the concave portion.

14. An implant according to claim 13, having a surface portion whose intersection with a first plane is concave and whose intersection with a second plane, perpendicular to the first plane, consists of said convex portion.

15. An implant according to claim 13, having a first surface portion whose intersection with a first plane is concave and whose intersection with a second plane, perpendicular to the first plane, consists of said convex portion, and a second surface portion whose intersection with the first plane is concave and whose intersection with the second plane consists of said concave portion.

16. An implant according to claim 15, further comprising a plane section in a third plane perpendicular to the first and second planes, having a substantially rectangular shape.

17. An implant according to claim 16, wherein said substantially rectangular shape has curved lateral edges.

18. An implant according to claim 1, having a plane section with a contour consisting of a convex portion and a substantially straight portion, wherein each end of the convex portion joins a corresponding end of the substantially straight portion.

19. An implant according to claim 18, having a surface portion whose intersection with a first plane is concave and whose intersection with a second plane, perpendicular to the first plane, consists of said convex portion.

20. An implant according to claim 18, having a first surface portion whose intersection with a first plane is concave and whose intersection with a second plane, perpendicular to the first plane, consists of said convex portion, and a second surface portion whose intersection with the first plane is concave and whose intersection with the second plane consists of said substantially straight portion.

21. An implant according to claim 20, further comprising a plane section in a third plane perpendicular to the first and second planes, having a substantially rectangular shape.

22. An implant according to claim 21, wherein said substantially rectangular shape has curved lateral edges.

23. An implant according to claim 1, comprising a first surface portion whose intersection with a first plane is concave and whose intersection with a second plane, perpendicular to the first plane, is convex, and a second surface portion, opposite the first surface portion, whose respective intersections with the first and second planes are convex.

24. An implant according to claim 23, further comprising a third surface portion whose respective intersections with the second plane and a third plane, perpendicular to the first and second planes, are concave, and a fourth surface portion, opposite the third surface portion, whose respective intersections with the second and third planes are concave, wherein the third and fourth surface portions connect the first and second surface portions to each other.

25. An implant according to claim 24, having a flat shape in said second and third planes.

26. An implant according to claim 23, further comprising a third surface portion whose respective intersections with the second plane and a third plane, perpendicular to the first and second planes, are convex, and a fourth surface portion, opposite the third surface portion, whose respective intersections with the second and third planes are convex, wherein the third and fourth surface portions connect the first and second surface portions to each other.

27. An implant according to claim 26, having a flat shape in said second and third planes.

28. An implant according to claim 1, having a substantially oval first plane section, a substantially rectangular second plane section, perpendicular to the first plane section, and a third plane section, perpendicular to the first and second plane sections, having a convex contour portion and a concave contour portion opposite the convex contour portion.

29. Use of an implant according to claim 1 as one of the following joints: an interphalangeal joint, a metacarpo-phalangeal joint, a trapezio-metacarpal joint, a radio-carpal joint, a carpo-metacarpal joint, and a metatarso-phalangeal joint.

30. Use of an implant according to claim 1 as one of the following prostheses: a partial scaphoid prosthesis, a total wrist prosthesis, a partial wrist prosthesis, an ankle prosthesis, and an intervertebral disc prosthesis.

31. An implant having at least one contact surface portion designed to be in direct mobile contact with at least one bony surface when said implant is implanted in a patient, wherein said implant is made of a material having a Young's modulus approximately comprised between 10 and 35 GPa, and wherein said implant is free from any attaching means, so that said implant remains free with respect to said patient's bones when implanted in said patient.

32. An implant according to claim 31, having an external surface which remains free with respect to said at least one bony surface when implanted in said patient.

33. An implant according to claim 31, having a polished external surface.

* * * * *